(12) United States Patent
Müller et al.

(10) Patent No.: US 10,034,841 B2
(45) Date of Patent: *Jul. 31, 2018

(54) TRANSDERMAL THERAPEUTIC SYSTEM COMPRISING AN ADHESIVE LAYER METHOD FOR SILICONIZING THE BACK LAYER OF THE SYSTEM AND USE OF SAID BACK LAYER

(71) Applicant: LTS LOHMANN THERAPIE-SYSTEME AG, Andernach (DE)

(72) Inventors: Walter Müller, Andernach (DE); Johannes Leonhard, Bendorf (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,789

(22) Filed: Nov. 30, 2015

(65) Prior Publication Data
US 2016/0074336 A1    Mar. 17, 2016

Related U.S. Application Data

(63) Continuation of application No. 11/661,530, filed as application No. PCT/EP2005/009547 on Sep. 6, 2005, now Pat. No. 9,226,903.

(30) Foreign Application Priority Data

Sep. 13, 2004  (DE) ........................ 10 2004 044 578

(51) Int. Cl.
 *A61K 9/70* (2006.01)
 *A61F 13/02* (2006.01)

(52) U.S. Cl.
 CPC ............ *A61K 9/7069* (2013.01); *A61F 13/02* (2013.01); *A61F 13/023* (2013.01); *A61F 13/0253* (2013.01); *A61K 9/7084* (2013.01); *A61F 13/0246* (2013.01)

(58) Field of Classification Search
 None
 See application file for complete search history.

(56) References Cited

U.S. PATENT DOCUMENTS

| | | | |
|---|---|---|---|
| 4,481,341 A | 11/1984 | Schlak et al. | |
| 4,806,341 A | 2/1989 | Chien et al. | |
| 4,956,231 A | 9/1990 | Cavezzan et al. | |
| 6,261,595 B1 | 7/2001 | Stanley et al. | |
| 6,488,959 B2 | 12/2002 | Stanley et al. | |
| 2003/0180468 A1* | 9/2003 | Cray | C09D 183/04 427/387 |
| 2004/0057985 A1 | 3/2004 | Bracht | |
| 2004/0202710 A1 | 10/2004 | Muller | |
| 2005/0282977 A1 | 12/2005 | Stempel et al. | |

FOREIGN PATENT DOCUMENTS

| | | |
|---|---|---|
| EP | 1 191 927 B1 | 3/2003 |
| WO | WO 99/11265 A1 | 3/1999 |
| WO | WO 01/01967 A1 | 1/2001 |
| WO | WO 01/74338 A1 | 10/2001 |
| WO | WO 2004/069286 A2 | 8/2004 |
| WO | WO 2004/089361 A1 | 10/2004 |
| WO | WO 2005/063890 A2 | 7/2005 |

* cited by examiner

*Primary Examiner* — David J Blanchard
*Assistant Examiner* — Daniel F Coughlin
(74) *Attorney, Agent, or Firm* — ProPat, L.L.C.

(57) ABSTRACT

The invention generally relates to a transdermal therapeutic system which comprises a backing layer, an adhesive layer, a polymer layer and a removable protective layer. The adhesive layer is an organosiloxane layer that is anchored to the backing layer by siliconization.

11 Claims, 1 Drawing Sheet

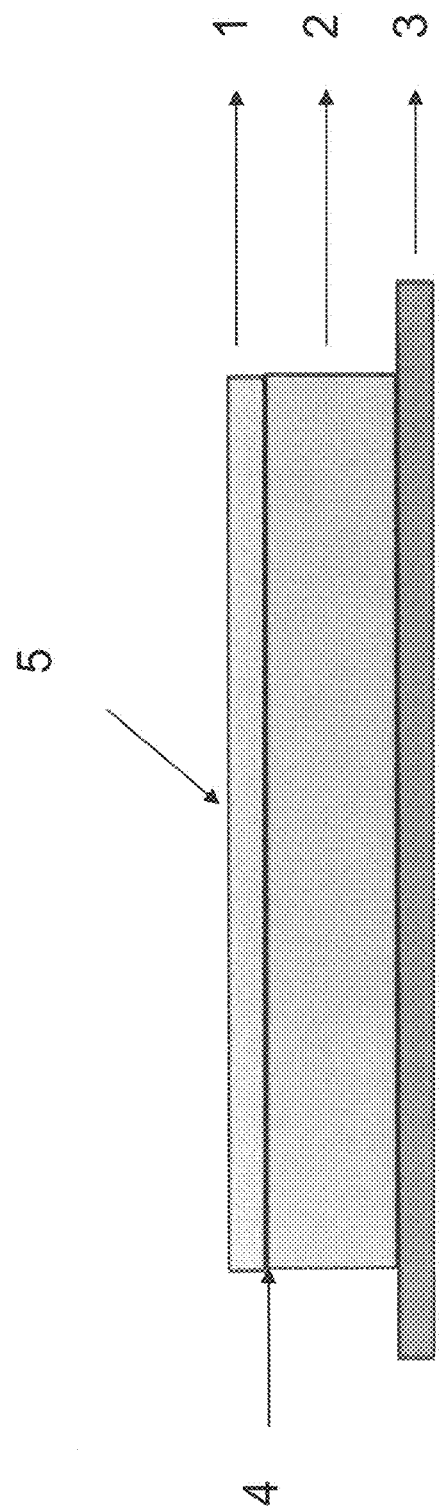

TRANSDERMAL THERAPEUTIC SYSTEM COMPRISING AN ADHESIVE LAYER METHOD FOR SILICONIZING THE BACK LAYER OF THE SYSTEM AND USE OF SAID BACK LAYER

CROSS-REFERENCE TO RELATED APPLICATIONS

This application is a continuation application of allowed U.S. application Ser. No. 11/661,530, filed Feb. 27, 2007, which was a national stage application of International Application No. PCT/EP2005/009547 filed Sep. 6, 2005, which claims priority to German Patent Application No. 10 2004 044 578.8, filed Sep. 13, 2004. Each of parent U.S. application Ser. No. 11/661,530, International Application No. PCT/EP2005/009547 and German Patent Application No. 10 2004 044 578.8 are hereby incorporated by reference herein in their entirety.

FIELD OF THE INVENTION

The invention relates to a transdermal therapeutic system comprising a hacking layer, a polymer layer in contact with the backing layer and comprising silicone adhesives, and a detachable protective layer in contact with the polymer layer, to a method of producing a siliconized backing layer of the system, and to the use of the backing layer.

BACKGROUND OF THE INVENTION

Transdermal therapeutic systems (TTS) or active ingredient patches have now become an established drug form. In spite of this, certain problems associated with this drug form have to date not been solved to satisfaction. One of these problems relates specifically to the so-called matrix systems or systems which have a construction related to the matrix systems. A matrix system of this kind, or matrix TTS, is composed at its most simple of a backing layer, an active ingredient matrix layer, preferably self-adhesive, and a protective layer, which is intended for removal prior to use. Oftentimes, during wearing of the TTS, after a certain time the formation of a more or less weak dark margin around the patch on the skin is observed, and/or residues of adhesive remain on the skin when the TTS is removed. This phenomenon is observed to a particularly marked extent in the case of TTS suitable for application for a number of days. The cause of both phenomena is inadequate adhesion of the patch matrix to the backing layer of the system. This inadequate adhesion, and movements of the body at the site of application, cause the adhesive to emerge at the edges of the system, and the adhesive which has emerged may come into contact with the clothing. As a result of contact with the clothing, fabric fibers remain suspended from the emerged adhesive and impart to it in the majority of cases a dark appearance. Following the removal of the TTS, the adhesive which has emerged remains on the skin in the form of dark marks. If adhesion to the backing layer is particularly poor, the matrix may also part over a substantial area from the backing layer, and may remain on the skin. Particularly susceptible to such phenomena are adhesives based on silicones. The reason for this is that silicone adhesives are very apolar and therefore adhere relatively poorly to the more or less polar surfaces of the backing layer, which in the majority of cases is composed of polyethylene terephthalate (PET). A further factor is that the cohesion possessed by silicone adhesives is low and therefore they have a particularly strongly pronounced tendency to emerge from the system. Silicone adhesives therefore behave like a viscous liquid, and the spreading over a relatively large area is hence also referred to as "cold flow".

SUMMARY OF ADVANTAGEOUS EMBODIMENTS OF THE INVENTION

It is an object of the present invention, accordingly, to improve the adhesion of the backing layer in a transdermal therapeutic system to the active ingredient polymer layer which comprises at least one silicone adhesive, and largely to prevent the emergence of silicone adhesive from the system.

DETAILED DESCRIPTION OF THE DRAWINGS

FIG. 1 schematically illustrates an exemplary inventive transdermal therapeutic system.

DETAILED DESCRIPTION OF ADVANTAGEOUS EMBODIMENTS OF THE INVENTION

This object is achieved in accordance with the invention by a transdermal therapeutic system as described at the outset by providing the contact face of the backing layer with an adhesive layer obtained by siliconization.

In embodiment of the invention the adhesive layer is an organopolysiloxane layer. In particular the adhesive layer comprises organopolysiloxanes containing vinyl groups and organopolysiloxanes containing Si—H groups.

In a preferred way the backing layer is a polymeric film material selected from the group consisting of polyesters, especially polyethylene terephthalate, polypropylene, polyethylene, polyurethane, EVA layers in combination with polyester, polyvinylidene chloride, polyaramid, and ethylene-(meth)acrylate copolymers.

The further embodiment of the invention is evident from the features of claims 5 to 9.

The method of the invention, namely a method of producing a backing layer used in a transdermal therapeutic system, is distinguished by the fact that it comprises siliconizing the surface of the backing layer that is to be contacted with a polymer layer which has been provided with microreservoirs. This is accomplished preferably by mixing organopolysiloxanes containing vinyl groups and organopolysiloxanes containing functional Si—H groups and coating the surface of the backing layer with the mixture in the presence of a catalyst. Thereafter the coated surface of the backing layer is heat-treated until an organopolysiloxane layer forms that is firmly anchored on the backing layer. The catalyst used is, for example, a platinum catalyst. The heat treatment takes place in a thermal oven or in a thermal tunnel. The temperature is about 80 to 100° C., but can also be below 80° C.

Any self-adhesive system, whether it be a transdermal therapeutic system, a non-active ingredient patch (plaster), a label or an adhesive tape, must be protected prior to use by a protective layer which can be redetached. The protective layer may be composed of various materials such as PET, polyethylene or polypropylene, for example, and on the adhesive contact side has been treated specifically in order to make it detachable from the adhesive layer as easily as possible. For use in combination with adhesives not based on silicones, this surface treatment usually consists of a siliconization. This siliconization involves coating, for example, organopolysiloxanes containing vinyl groups and organopolysiloxanes containing SiH-functional groups in a mixture onto the film that is to be treated, in a coating operation in the presence of a platinum catalyst, with a heat treatment resulting in formation of an organopolysiloxane layer that adheres firmly to the substrate. Whereas non-silicone-based adhesives, such as polyacrylate adhesives, for example, attach extremely poorly to surfaces thus treated, silicone adhesives attach extremely well to such surfaces. In plaster-wearing tests it has been found that non-active ingredient patches based on silicone adhesives and a backing layer treated in this manner leave considerably lesser/fewer adhesive residues on the skin following removal, and that the tendency toward formation of "black" margins around the patch is considerably reduced.

In the case of TTS based on silicone adhesives, the permeation rate of the active ingredient through the skin is increased by the external application of heat to the applied TTS. Systems of this kind are described in detail in, for example, U.S. Pat. No. 6,488,599 A1 and U.S. Pat. No. 6,261,595 A1. As a result of the temperature, which in this context can easily climb up to about 45° C., the tendency of the silicone adhesive to spread by cold flow is massively increased. Under such conditions it is more likely that dark edges will form around the patch and that adhesive residues will be left on the skin following the removal of the patch. In such systems great advantage attaches to siliconizing the backing layer, since despite the application of heat the spreading of the adhesive is largely prevented.

The siliconization of the backing layer likewise proves particularly important for the active ingredient in conjunction with systems of the kind known as microreservoir systems based on silicone adhesives and ambiphilic solvents. Microreservoir systems of this kind are described in detail in EP 1 191 927 B1. In the production of such systems the active ingredient is dissolved in an ambiphilic solvent such as dipropylene glycol or 1,3-butanediol, for example, and the solution is dispersed in the solution of the adhesive. Thereafter the dispersion is coated onto the protective layer of the subsequent TTS, the solvent of the adhesive is removed, and the dried film is laminated to the backing layer. It has now emerged that an unsiliconized backing layer exhibits virtually no adhesion to such a film. The reason for this is the formation of a very thin film of the ambiphilic solvent on the surface of the dried active ingredient film. Altering the production method, e.g., coating directly onto the backing layer, does not improve the adhesion of the dried film. A siliconized backing layer, however, irrespective of the chemical nature of the film material itself, produces very good adhesion immediately after contact with a microreservoir layer. Although improved adhesion can also be achieved through the use of materials which are less inert, such as copolymers of ethylene and vinyl acetate, for example, for the backing layer of such systems, materials of this kind have the drawback that they absorb active ingredient as well as the solvent. Microreservoir systems as described above are therefore best realizable using siliconized backing layers of polyester or similarly inert materials.

The single FIGURE, FIG. 1, shows a transdermal therapeutic system 5 which comprises a backing layer 1, an adhesive layer 4 firmly anchored on the backing layer, a polymer layer 2, and a detachable protective layer 3. The adhesive layer 4 is an organopolysiloxane layer which comprises organopolysiloxanes containing vinyl groups and organopolysiloxanes containing functional Si—H groups. The backing layer 1 is composed of a polymeric film material. Suitable polymers are polyesters, especially polyethylene terephthalate, polypropylene, polyethylene, polyurethane, EVA layers in combination with polyester, PVDC, polyaramids, and ethylene(meth)acrylate copolymers. Further suitable materials are ethylcellulose, cellulose acetate, cellophane, paper, metal-polymer composite, and ethylene-vinyl acetate copolymers.

The silicone adhesives in the polymer layer 2 are selected for example from the group consisting of polysiloxanes and polysiloxane mixtures.

Present in the polymer layer 2 are microreservoirs which contain at least one active ingredient which is in solution in an ambiphilic solvent. Suitable ambiphilic solvents are 1,3-butanediol, diethylene glycol monomethyl ether, diethylene glycol dimethyl ether, dipropylene glycol, propylene glycol, tetrahydrofurfuryl alcohol, diethylene glycol monobutyl ether, carboxylic esters of tri- and diethylene glycol, and polyoxyethylated fatty alcohols of 6-18 carbon atoms.

The protective layer 3 overhangs both sides of the polymer layer 2, so that it can be grasped and detached without problems.

The use of a siliconized backing layer has no influence whatsoever on the production of microreservoir systems. Even in the case of TTS already on the market, it is possible from a purely technical standpoint to replace the non-siliconized backing layer without problems by a siliconized backing layer. The properties of the TTS in respect of active ingredient delivery remain unaffected in the case of such replacement, since with a thickness of less than 10 micrometers the applied silicone layer absorbs virtually no active ingredient.

In summary, therefore, it can be stated that the use of siliconized backing layers decisively improves the wear properties of TTS based on silicone adhesives, and now makes specific systems, such as microreservoir systems based on silicone adhesives and ambiphilic solvents, for example, technically feasible.

That which is claimed is:

1. A transdermal therapeutic system comprising in spatial order
    (a) a backing layer,
    (b) a siliconized anchor layer, and
    (c) a polymer layer comprising at least one silicone adhesive acid active ingredient,
    wherein said siliconized anchor layer (b)
    (i) is firmly anchored to the backing layer (a),
    (ii) adheres to the polymer layer (c),
    (iii) comprises organopolysiloxanes containing vinyl groups crosslinked with organopolysiloxanes containing Si—H groups, and
    (iv) has a thickness of less than 10 micrometers.

2. The transdermal therapeutic system as claimed in claim 1, wherein the backing layer is a polymeric film material selected from the group consisting of polyesters, polypropylene, polyethylene, polyurethane, EVA layers in combination with polyester, polyvinylidene chloride, polyaramids, and ethylene-(meth)acrylate copolymer.

3. A transdermal therapeutic system as claimed in claim 2, wherein the polymeric film material is polyethylene terephthalate.

4. The transdermal therapeutic system as claimed in claim 1, wherein the backing layer comprises a material selected from the group consisting of ethylcellulose, cellulose acetate, cellophane, paper, metal-polymer composite, and ethylene-vinyl acetate copolymers.

5. The transdermal therapeutic system as claimed in claim 1, wherein the silicone adhesive is selected from the group consisting of polysiloxanes and polysiloxane mixtures.

6. A transdermal therapeutic system as claimed in claim 1, wherein said polymer layer (c) is self-adhesively connected to the siliconized anchor layer (b).

7. A transdermal therapeutic system as claimed in claim 1, wherein said system further comprises a detachable protective layer.

8. A transdermal therapeutic system as claimed in claim 1, wherein said siliconized anchor layer absorbs no active ingredient.

9. A transdermal therapeutic system as claimed in claim 1, wherein said backing layer is polar, said polymer layer consists of silicone adhesive, and said adhesive does not extend past said transdermal therapeutic system.

10. A transdermal therapeutic system as claimed in claim 1, wherein said siliconized anchor layer consists of organopolysiloxanes containing vinyl groups and organopolysiloxanes containing Si—H groups.

11. The transdermal therapeutic system as claimed in claim 1, wherein said polymer layer (c) adheres to said detachable protective layer.

* * * * *

UNITED STATES PATENT AND TRADEMARK OFFICE
CERTIFICATE OF CORRECTION

PATENT NO. : 10,034,841 B2
APPLICATION NO. : 14/953789
DATED : July 31, 2018
INVENTOR(S) : Müller et al.

Page 1 of 1

It is certified that error appears in the above-identified patent and that said Letters Patent is hereby corrected as shown below:

In the Claims

Column 4
Claim 1, Line 46, delete "acid" insert --and--

Signed and Sealed this
Nineteenth Day of May, 2020

Andrei Iancu
*Director of the United States Patent and Trademark Office*